United States Patent
Chen et al.

(10) Patent No.: US 6,893,401 B2
(45) Date of Patent: May 17, 2005

(54) CONTINUOUS NON-INVASIVE BLOOD PRESSURE MONITORING METHOD AND APPARATUS

(75) Inventors: Yunquan Chen, Delta (CA); Luya Li, Coquitlam (CA); Cecil Hershler, Vancouver (CA); Ryan Peter Dill, Vancouver (CA)

(73) Assignee: VSM Medtech Ltd., Vancouver (CA)

( * ) Notice: Subject to any disclaimer, the term of this patent is extended or adjusted under 35 U.S.C. 154(b) by 0 days.

(21) Appl. No.: 10/438,676

(22) Filed: May 15, 2003

(65) Prior Publication Data

US 2003/0199770 A1 Oct. 23, 2003

Related U.S. Application Data

(63) Continuation of application No. 09/917,279, filed on Jul. 27, 2001, now Pat. No. 6,599,251.

(51) Int. Cl.[7] .................................................. A61B 5/02
(52) U.S. Cl. ........................ 600/485; 600/481; 600/500
(58) Field of Search ................................ 600/481, 485, 600/486, 490, 492–496, 500–503

(56) References Cited

U.S. PATENT DOCUMENTS

| | | |
|---|---|---|
| 3,790,910 A | 2/1974 | McCormack |
| 3,908,640 A | 9/1975 | Page |
| 4,245,648 A | 1/1981 | Trimmer et al. |
| 4,303,984 A | 12/1981 | Houvig |
| 4,404,974 A | 9/1983 | Titus |
| 4,492,877 A | 1/1985 | Staerzl |
| 4,718,427 A | 1/1988 | Russell |
| 4,718,428 A | 1/1988 | Russell |
| 4,873,987 A | 10/1989 | Djordjevich et al. |
| 4,907,596 A | 3/1990 | Schmid et al. |
| 5,033,472 A | 7/1991 | Sato et al. |
| 5,072,735 A | 12/1991 | Ogawa et al. |

(Continued)

FOREIGN PATENT DOCUMENTS

| | | |
|---|---|---|
| EP | 0 181 067 | 5/1986 |
| EP | 0 443 267 A1 | 8/1990 |
| EP | 0 456 844 A1 | 11/1991 |
| EP | 0 821 910 A2 | 2/1998 |
| EP | 0 829 227 A2 | 3/1998 |
| EP | 0 852 126 A2 | 7/1998 |
| EP | 0 875 200 A1 | 11/1998 |

(Continued)

OTHER PUBLICATIONS

A short article and a copy of a 510(k) Notification regarding Sentinel Monitoring, Inc.'s Artac™ 7000 Vital Signs Device, 1990 (a re–typed copy of pages 8 through 11 of the 510(k) Notification is enclosed).

A copy of *Monitoring in Anesthesia and Critical Care Medicine*, 1995, pp. 117–130.

*Primary Examiner*—Mary Beth Jones
*Assistant Examiner*—Navin Natnithithadha
(74) *Attorney, Agent, or Firm*—Oyen Wiggs Green & Mutala

(57) ABSTRACT

A non-invasive apparatus and method for monitoring the blood pressure of a subject detects a pulse signal at both a first and second location on the subject's body The elapsed time between the arrival of corresponding points of the pulse signal at the first and second locations is determined. Blood pressure is related to the elapsed time by relationships such as:

$$P = a + b \ln(T),$$

where a and b are constants dependent upon the nature of the subject and the signal detecting devices. The system can be calibrated by measuring a single pair of reference blood pressure and corresponding elapsed time

22 Claims, 11 Drawing Sheets

U.S. PATENT DOCUMENTS

| | | |
|---|---|---|
| 5,237,997 A | 8/1993 | Greubel et al. |
| 5,255,686 A | 10/1993 | Takeda et al. |
| 5,293,874 A | 3/1994 | Takahashi et al. |
| 5,309,916 A | 5/1994 | Hatschek |
| 5,485,838 A | 1/1996 | Ukawa et al. |
| 5,485,848 A | 1/1996 | Jackson et al. |
| 5,533,511 A | 7/1996 | Kaspari et al. |
| 5,564,427 A | 10/1996 | Aso et al. |
| 5,584,299 A | 12/1996 | Sakai et al. |
| 5,590,649 A | 1/1997 | Caro et al. |
| 5,603,329 A | 2/1997 | Hosaka et al. |
| 5,649,543 A | 7/1997 | Hosaka et al. |
| 5,676,140 A | 10/1997 | Ukawa et al. |
| 5,699,807 A | 12/1997 | Motogi et al. |
| 5,709,212 A | 1/1998 | Sugo et al. |
| 5,743,856 A * | 4/1998 | Oka et al. .................. 600/493 |
| 5,743,857 A | 4/1998 | Shinoda et al. |
| 5,752,920 A | 5/1998 | Ogura et al. |
| 5,755,669 A | 5/1998 | Ono et al. |
| 5,772,602 A | 6/1998 | Sakai et al. |
| 5,776,071 A | 7/1998 | Inukai et al. |
| 5,810,734 A | 9/1998 | Caro et al. |
| 5,833,618 A | 11/1998 | Caro et al. |
| 5,857,975 A | 1/1999 | Golub |
| 5,865,755 A | 2/1999 | Golub |
| 5,873,834 A | 2/1999 | Yanagi et al. |
| 5,876,348 A | 3/1999 | Sugo et al. |
| 5,882,311 A | 3/1999 | O'Rourke |
| 5,921,936 A | 7/1999 | Inukai et al. |
| 6,004,274 A | 12/1999 | Nolan et al. |
| 6,010,457 A | 1/2000 | O'Rourke |
| 6,083,171 A | 7/2000 | Ono et al. |
| 6,120,459 A * | 9/2000 | Nitzan et al. ................ 600/493 |
| 6,129,677 A | 10/2000 | Sohma et al. |
| 6,190,325 B1 | 2/2001 | Narimatsu |
| 6,368,282 B1 * | 4/2002 | Oka et al. .................. 600/485 |
| 6,599,251 B2 * | 7/2003 | Chen et al. .................. 600/485 |
| 6,616,613 B1 * | 9/2003 | Goodman .................. 600/504 |
| 2002/0002339 A1 | 1/2002 | Sugo et al. |

FOREIGN PATENT DOCUMENTS

| | | |
|---|---|---|
| EP | 0 852 126 A3 | 12/1998 |
| EP | 0 956 813 A1 | 11/1999 |
| EP | 0 956 815 A1 | 11/1999 |
| EP | 0 956 816 A1 | 11/1999 |
| JP | 07 136 136 | 5/1995 |
| JP | 08 131 410 | 5/1996 |
| JP | 9122087 A | 5/1997 |
| JP | 10 151 118 | 6/1998 |
| JP | 2000107141 | 4/2000 |
| WO | WO 89/08424 A | 9/1989 |
| WO | WO 00/10453 | 3/2000 |

* cited by examiner

CONTINUOUS NON-INVASIVE BLOOD PRESSURE MONITORING METHOD AND APPARATUS

REFERENCE TO RELATED APPLICATION

This application is a continuation application of U.S. patent application Ser. No. 09/917,279 filed on 27 Jul. 2001, now U.S. Pat. No. 6,599,251, which claims priority to U.S. provisional patent application No. 60/178,027 filed on 26 Jan. 2000 and of PCT international application No. PGT/CA00/01552 filed on 22 Dec. 2000 and entitled CONTINUOUS BLOOD PRESSURE MONITORING METHOD AND APPARATUS.

FIELD OF THE INVENTION

This invention relates to blood pressure monitoring devices of the type which measure transit times of pulses in a subject's blood circulatory system and compute an estimated blood pressure from the measured pulse transit times.

BACKGROUND OF THE INVENTION

Various approaches have been tried for monitoring the blood pressure of living subjects. One approach is to insert a pressure sensor directly into a suitable artery in the subject. The sensor can be Connected to a suitable monitoring device by a lead which passes through the subject's skin. This approach provides accurate and instantaneous blood pressure measurements. A disadvantage of this approach is that it is invasive. A surgical procedure is required to introduce the pressure sensor. The fistula through which the lead exits the subject's body can provide a pathway for infection.

Another approach to measuring blood pressure uses a sphygmomanometer. A typical sphygmomanometer has an occluding cuff capable of being wrapped around a subject's arm; a pump for inflating the cuff; either an aneroid or mercury gravity sphygmomanometer to measure pressure in the cuff; and a stethoscope or other system for detecting Korotkoff sounds. Such devices are widely used in hospitals and doctors' offices for making routine blood pressure measurements but are not well adapted to providing continuous blood pressure monitoring.

Another method for measuring blood pressure is the oscillometric method. Oscillometric blood pressure measurements are made by using a transducer to detect and measure pressure waves in a pressure cuff as blood surges through an artery constricted by the pressure cuff. Many currently available digital blood pressure monitors use the oscillometric method for determining blood pressure. The oscillometric method is not ideal for continuous blood pressure monitoring because it typically cannot produce an updated blood pressure reading more frequently than about once every 30 seconds. Further, the cuff compresses underlying tissues. Over an extended period of time this can cause tissue damage.

There has been significant research directed toward the development of new non-invasive techniques for monitoring blood pressure. One approach exploits the correlation between blood pressure and the time taken for a pulse to propagate from a subject is heart to a selected point on a subject's artery. This approach is possible because the speed at which pulse waves travel from the heart to points downstream in a subject's blood circulatory system varies with blood pressure. As blood pressure rises the propagation velocity of arterial pulse waves increases and the pulse transit time decreases. In general, such methods may be called Pulse Transit Time (or "PTT") methods. Typically a signal from an electrocardiogram (EKG) is used to detect a heart best and a pressure sensor is used to detect the arrival of a pulse wave generated by the heart beat at a downstream location. This approach is described, for example, by Inukai et al., U.S. Pat. No. 5,921,936. The Inukai et al. system uses an electrocardiogram to detect the start of a heart beat and uses a cuff equipped with a pressure sensor to detect pulse waves. Other similar systems are described in Orr et al., European Patent application No. EP0181067. A variation of this approach is described in Golub, U.S. Pat. No. 5,87,975.

One difficulty with PTT blood pressure measurement systems which measure blood pressure as a function of the time between the pulse of an EKG signal and a detected pulse wave is that there is a delay between the onset of an EKG pulse and the time that the heart actually begins to pump blood. This delay can vary significantly in a random way, even in healthy subjects. Hatschek, U.S. Pat. No. 5,309,916 discloses a method for measuring blood pressure by determining the time taken for a pulse to propagate downstream along a single arterial branch. This approach eliminates uncertainties caused by the imperfect correlation between EKG signals and the delivery of blood by the heart. However, it has the disadvantage that it can be difficult to arrange two sensors so that they can detect a pulse at each of two widely spaced apart locations along a single arterial branch.

Another difficulty with prior art PTT blood pressure measurements is that the relationship between blood pressure and the time taken for pulses to transit a portion of the blood circulatory system is different for every subject. Thus, it is necessary to calibrate a ITT blood pressure measurement system for each subject.

The book entitled *Monitoring in Anesthesia and Critical Care Medicine*, 3rd Edition, edited by Blitt and Hines, Churchill Livingstone, 1995, mentions a blood pressure monitor having the trade name, ARTRAC™ 7000 which used two photometric sensors, one on the ear and another on a finger, to measure diastolic blood pressure. This device apparently used the difference in arrived times of pulses at the ear and finger to measure the pulse transit time. The diastolic pressure was estimated based on a relationship of pressure and pulse wave velocity. This device apparently computed systolic pressure from the pulse volume. Further information about this device is provided in a FDA 510 (k) Notification entitled, "ARTRAC™ Vital Sign Monitor, Models 7000 and 5000 (K904888)," submitted by Sentinel Monitoring, Inc., 1990.

A relationship between blood pressure and pulse transit time can be developed by assuming that an artery behaves as if it were a thin-walled elastic tube. This relationship, which is known as the Moens-Korteweg-Hughes equation is described in more detail below. The Moens-Korteweg-Hughes equation depends on the elasticity and geometry of blood vessels and is highly nonlinear.

Inventors Aso et al., U.S. Pat. No. 5,564,427, proposed the use of a linear equation to calculate blood pressure using the EKG based pulse transit time. This method was further developed by Hosaka et al., U.S. Pat. No. 5,649,543. To calibrate the linear measurement system, Sugo et al., U.S. Pat. No. 5,709,212, introduced a multi-parameter approach to determine the parameters at deferent blood pressure levels for systolic and diastolic pressures respectively. Shirasaki patented another method to calibrate the parameters based on the multiple blood pressure reference inputs in Japanese patent No. 10-151118.

Despite progress that has been made in the field of blood pressure measurement, there remains a need for devices for blood pressure measurement which have acceptable accuracy and do not require complicated calibration steps.

SUMMARY OF THE INVENTION

This invention provides blood pressure measurement methods and apparatus which avoid some of the disadvantages of the prior art. Preferred embodiments of the invention are suitable for continuous non-invasive blood pressure ("CNIBP") monitoring.

One aspect of the invention provides methods for monitoring blood pressure. The method comprises detecting a first pulse signal at a first location on a subject and detecting a second pulse signal at a second location on the subject; measuring a time difference between corresponding points on the first and second pulse signals; and, computing an estimated blood pressure from the time difference.

In preferred embodiments of the invention, computing an estimated blood pressure comprises performing the calculation:

$$P = a + b \ln(T)$$

where P is the estimated blood pressure, a is a constant, b is a constant, and T is the time difference. Most preferably, the constants a and b for a particular subject are determined by performing a calibration by taking a reference blood pressure reading to obtain a reference blood pressure $P_0$, measuring the elapsed time $T_0$ corresponding to the reference blood pressure and determining values for both of the constants a and b from $P_0$ and $T_0$.

Accordingly, a method for monitoring blood pressure according to one aspect of the invention comprises: detecting a first pulse signal at a first location on a subject and detecting a second pulse signal at a second location on the subject; measuring a reference blood pressure $P_0$ and a corresponding time difference $T_0$ between the first and second pulse signals; from the reference blood pressure and corresponding time difference, determining a first plurality of constant parameters in a multi-parameter equation relating blood pressure and the time-difference; monitoring the subject's blood pressure by periodically measuring a time difference T between the first and second pulse signals; computing an estimated blood pressure, P, from the time difference, T, using the multi-parameter equation and the first plurality of constant parameters.

The multi-parameter equation may be the calculation:

$$P = a + b \ln(T)$$

or a mathematical equivalent thereof where a and b are constants.

In some specific embodiments, determining the plurality of constant parameters in the multi-parameter equation comprises performing calculations mathematically equivalent to:

$$a = c_1 + \frac{c_2(P_0 - c_1)}{\ln(T_0) + c_2} \quad \text{and,}$$

$$b = \frac{P_0 - c_1}{\ln(T_0) + c_2}$$

to obtain values for the constants a and b, where $c_1$ and $c_2$ are predetermined constants.

In other specific embodiments of the invention determining the plurality of constant parameters in the multi-parameter equation comprises performing calculations mathematically equivalent to:

$$a = P_0 - (c_3 T_0 + c_4) \ln(T_0), \text{ and}$$

$$b = c_3 T_0 + c_4$$

where a and b are first and second parameters and $c_3$ and $c_4$ are predetermined constants.

In preferred embodiments of the invention the multi-parameter equation comprises a non-linear function which is monotonically decreasing and concave upward in a manner specified by the constant parameters.

The invention may be applied to measuring systolic blood pressures of subjects. In preferred embodiments of the invention measuring the time difference T comprises measuring a first time difference $T_S$ for higher portions (i.e. portions corresponding generally to the parts of the signals associated with systolic blood pressure) of the first and second signals. Measuring the first time difference may comprise maximizing a cross-correlation between the first and second pulse signals. Preferably, in such measurements portions of the first and second pulse signals below a first threshold are not considered. The first threshold may be an average value for the signal (or equivalently a mean value for the signal).

Another aspect of the invention provides a method for estimating a blood pressure of a subject. The method comprises detecting a pulse signal at a first location; detecting the pulse signal at a second location; determining an elapsed time, T, between the arrival of corresponding points of the pulse signal at the first and second locations; and, computing an estimated blood pressure, P, from the elapsed time by performing the calculation:

$$P = a + b \ln(T)$$

where a and b are constants.

Yet another aspect of the invention provides a method for estimating the blood pressure, P, of a subject. The method comprises: detecting a first pulse signal at a first location; detecting a second pulse signal at a second location; performing a calibration by measuring the subject's blood pressure $P_0$ and measuring a corresponding elapsed times $T_0$, between the arrival of corresponding points of the first and second pulse signals; subsequently monitoring the subject's blood pressure by determining an elapsed time, T, between the corresponding points of the first and second pulse signals; and, calculating an estimated blood pressure, P, based on the value:

$$\frac{(P_0 - c_1)}{(\ln(T_0) + c_2)}$$

where $c_1$ and $c_2$ are constants.

A still further aspect of the invention provides a method for estimating the blood pressure, P, of a subject. The method comprises; detecting a first pulse signal at a first location; detecting a second pulse signal at a second location; performing a calibration by measuring the subject's blood pressure $P_0$ and measuring a corresponding elapsed time, $T_0$, between corresponding points of the first and second pulse signals; subsequently monitoring the subject's blood pressure by determining an elapsed time, T, between corresponding points of the first and second pulse signals; and, calculating an estimated blood pressure, P, substantially according to the equation:

$$P = P_0 + (c_3 T_0 + c_4) \ln(T/T_0)$$

where $c_3$ and $c_4$ are constants.

Yet another aspect of the invention provide; a method for estimating the blood pressure, P, of a subject. The method comprises: detecting a first pulse signal at a first location; detecting a second pulse signal at a second location; measuring a reference blood pressure $P_0$ and measuring a corresponding time difference, $T_0$, between corresponding points of the first and second pulse signals; from the reference blood pressure and corresponding time difference, determining a plurality of constant parameters in a multi-parameter equation relating blood pressure and the time difference by: determining a first parameter of the plurality of parameters as a predetermined function of the corresponding time difference; and, determining a second parameter of the plurality of parameters as a predetermined function of the reference blood pressure and the time difference; and, subsequently monitoring the subject's blood pressure by determining a time difference, T, between corresponding points of the first and second pulse signals and computing an estimated blood pressure from the time difference T using the multi-parameter equation and the first and second parameters.

Other aspects of the invention provide apparatus for making blood pressure measurements. One such aspect of the invention provides apparatus for estimating a blood pressure of a subject. The apparatus comprises a computer processor; an input for receiving a first signal corresponding to a pulse Signal detected at a first location; an input for receiving a second signal corresponding to the pulse signal detected at a second location; a program store containing computer software comprising instructions which, when run on the processor cause the processor to measure an elapsed time, T, between corresponding points on the first and second signals and compute an estimated blood pressure, P, from the elapsed time by performing the calculation:

$$P = a + b \ln(T)$$

where a and b are constants.

Another apparatus-related aspect of the invention provides apparatus for estimating a blood pressure of a subject. The apparatus comprises: signal detection means for detecting first and second pulse signals; correlation means for determining an elapsed time, T, between the first and second pulse signals; computation means for computing an estimated blood pressure, P, from the elapsed time according to a non-linear function which is generally decreasing and concave upward in a manner specified by two or more settable parameters; calibration means for receiving a reference blood pressure and associating the reference blood pressure with an elapsed time determined by the correlation means; and, means responsive to the calibration means for establishing values for the two or more settable parameters from the reference blood pressure and elapsed time.

A still further aspect of the invention provides a program product comprising a medium bearing computer-readable signals. The signals contain instructions which, when executed on a computer processor, cause the computer processor to perform a method according to the invention.

Further advantages and features of the invention are described below.

BRIEF DESCRIPTION OF THE DRAWINGS

In drawings which illustrate non-limiting embodiments of the invention.

DETAILED DESCRIPTION

Figure 1:
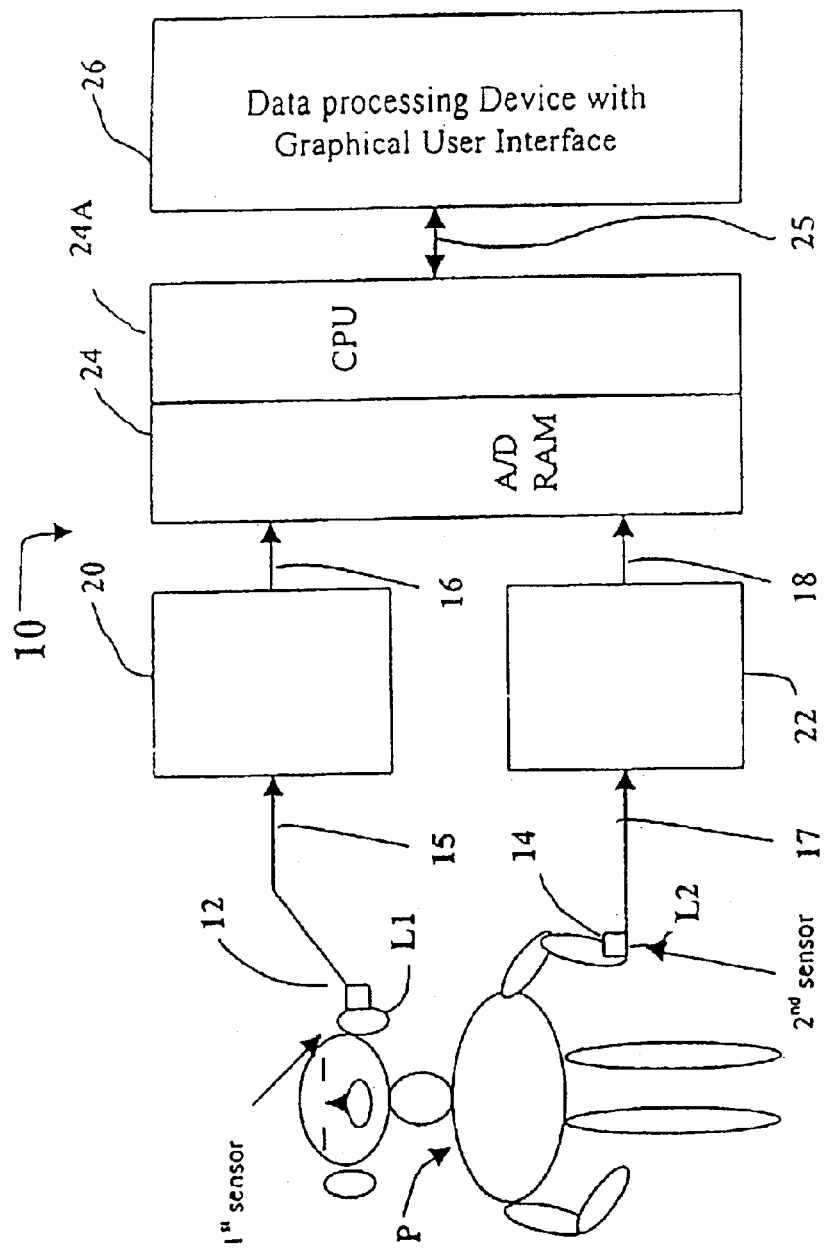
FIG. 1 is a block diagram of apparatus according to the invention.
Figure 2:
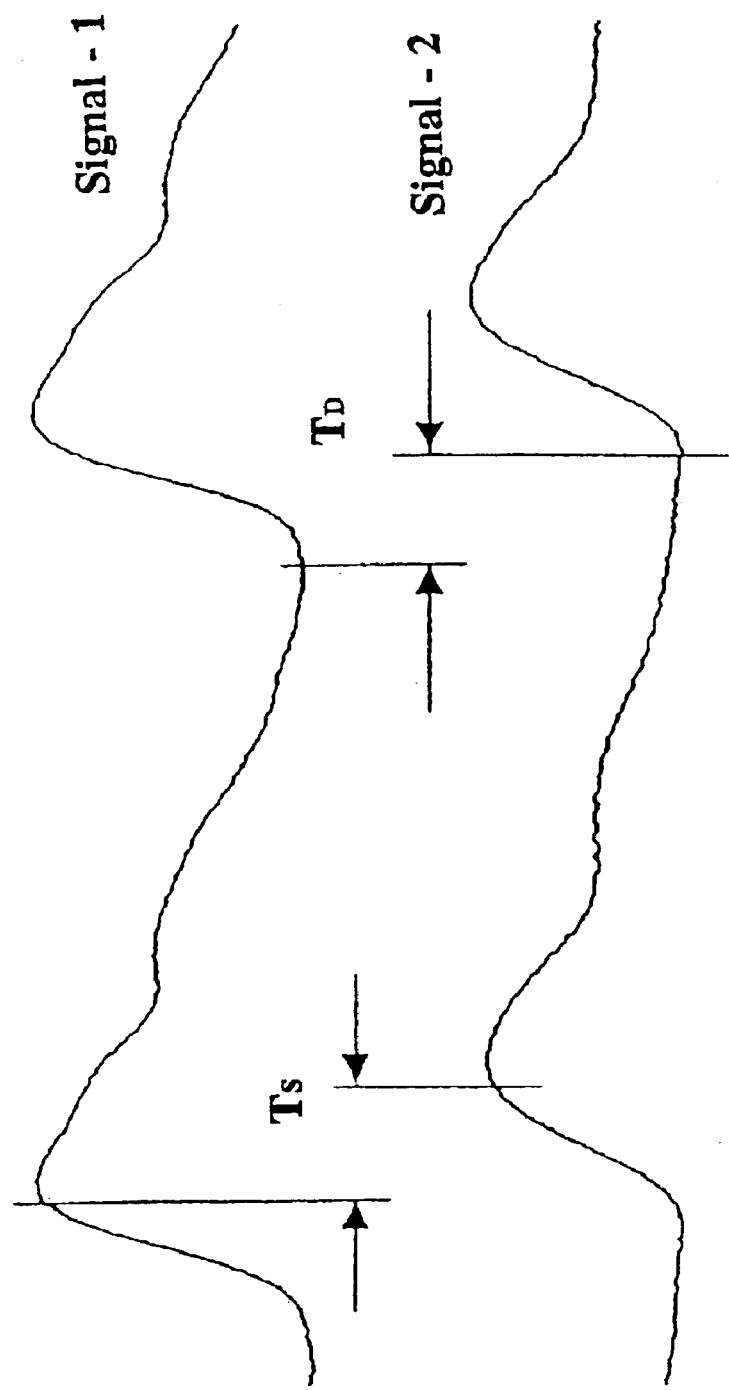
FIG. 2 is a diagram illustrating first and second pulse signals detected by the apparatus of FIG. 1.

The methods of the invention use the difference in transit times of pulse waves to different points on a subject's anatomy to measure blood pressure. As such, such methods may be called differential pulse transit time ("DPTT") methods FIG. 1 shows a blood pressure monitoring system 10 according to the invention. System 10 has an input sub-system comprising first and second sensors 12 and 14 which are each capable of detecting a pulse signal at a location on a subject. FIG. 2 depicts typical pulse signals 16 and 18. Sensors 12 and 14 can advantageously be photo-electric pulse wave sensors of a type used for pulse oximetry. An example of such a sensor is the model SAS-F FingerSat™ sensor available from Datex-Ohmeda (Canada) Incorporated. Sensors of this type are easy to obtain, reasonable in cost, light in weight and familiar to medical professionals.

Figure 4:
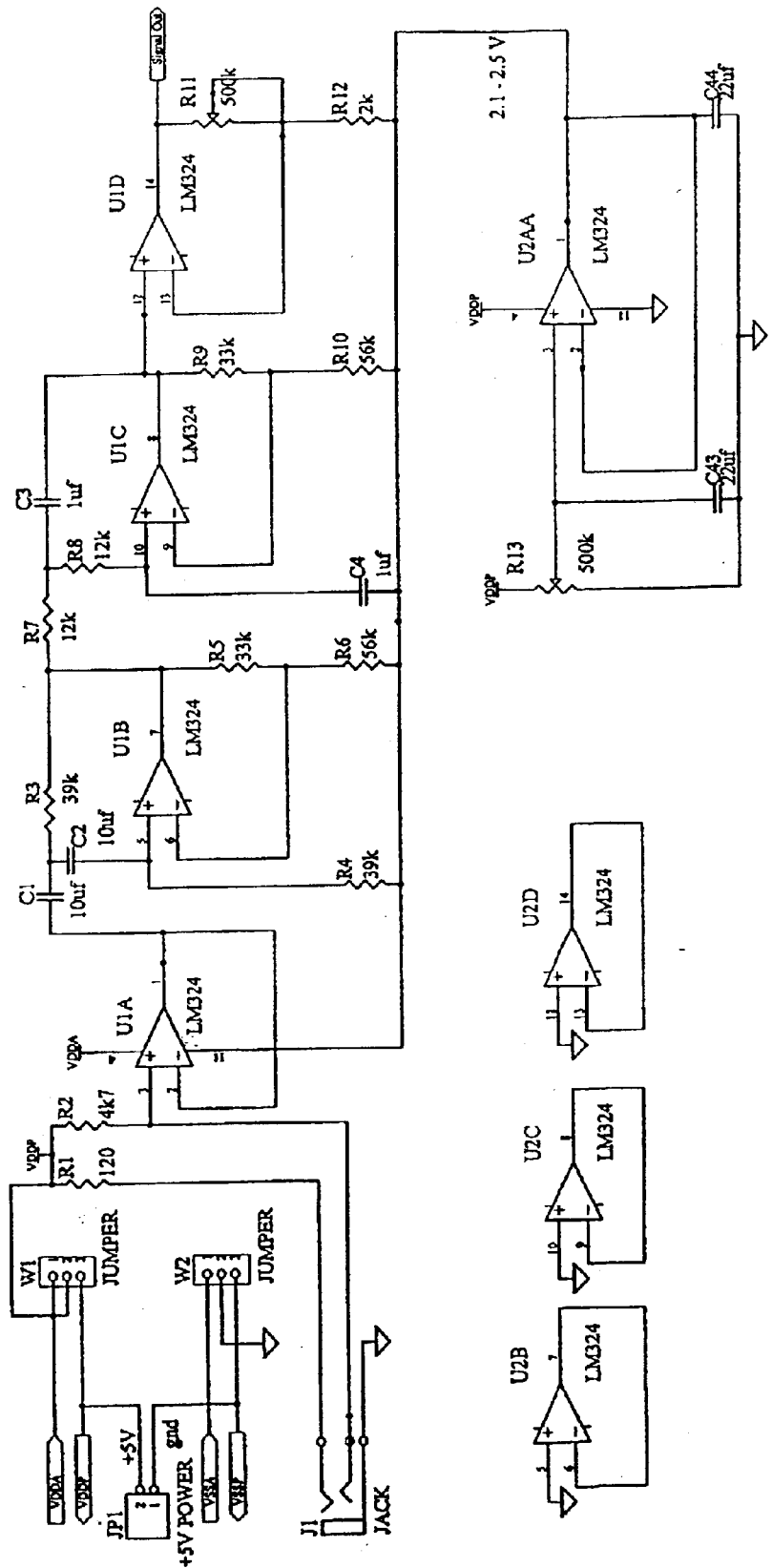
FIG. 4 is a schematic diagram of a possible sensor and signal-conditioning circuit for use in the invention.

Other types of sensor capable of detecting the arrivals of pulse waves at a location on a subject may also be used within the broad scheme of the invention. For example, FIG. 4 is a schematic diagram of a specific sensor implementation in which an OP140A light emitting diode available from Optech Technology Inc. is used to generate light. The light is reflected back to a model OP550A phototransistor also available from Optech Technology Inc. The remaining circuitry shown in FIG. 4 is an example of one possible embodiment for signal conditioning circuitry which could be used in the practise of this invention.

Other types of sensors which are capable of generating a signal representing the arrivals of pulses at different locations on a subject's body could also be used. Some examples of such other types of sensors are ultrasound sensors, tonometric sensors, and oscillometric cuffs.

Sensors 12 and 14 are applied to first and second locations L1 and L2 on a subject P. In the example illustrated in FIG. 1, L1 is an earlobe of the subject and L2 is a finger of the subject. L1 and L2 may be any places on a subject where pulse signals can be readily detected by sensors 12 and 14 respectively. L1 and L2 should be chosen so that a pulse wave (which originates at the subject's heart) takes a different amount of time to propagate to L1 than the pulse wave takes to propagate to L2. L1 and L2 can conveniently each be any of a finger, a toe, a wrist, an earlobe, an ankle, a nose, a lip, or any other part of the body where blood vessels are close to the surface of the skin. Most preferably, L1 and L2 are the paired combination of:

an earlobe and a finger;

an earlobe and a toe; or, a finger and a toe.

In preferred embodiments of the invention, L1 and L2 are supplied by blood from different branches of the subject's arterial system so that L1 is not directly downstream from L2 and L2 is not directly downstream from L1.

Since locations L1 and L2 do not need to be supplied by blood by the same branch of a subject's arterial system, this invention provides a much wider and more convenient range of locations for the application of sensors 12 and 14 than would be the case if sensor 12 was required to be directly upstream or downstream from sensor 14.

First and second electrical signals 15 and 17 are generated at sensors 12 and 14 respectively. Signals 15 and 17 are respectively conditioned by signal conditioning circuits 20 and 22. Signal conditioning circuits 20 and 22 preferably include low-pass filters to eliminate spurious spikes, noise filters to eliminate interference from power supplies and other noise sources, and gain amplifiers. After being conditioned, first and second signals 16 and 18 are digitized by an analog-to-digital converter ("ADC") 24. A single ADC 24 may be used to digitize both signals 16 and 18. Separate ADC's could also be used for signals 16 and 18.

Preferably each of signals 16 and 18 is sampled at a frequency of about 1 kHz, or greater. Most preferably the sampling frequency is 2 kHz or greater. If a sampling frequency of less than 1 kHz is used, interpolation of the sampled data is preferred used o achieve an effective sampling resolution of 1 millisecond or higher. ADC 24 can conveniently comprise an ADC integrated with a processor 24A capable of forwarding digitized signals 16 and 18 to data processing device 26 through a suitable data communication interface 25 for further analysis. For example, ADC 24 may comprise the 8/10 bit ADC portion of a Motorola MC68HC916X1 microcontroller.

FIG. 2 shows first and second signals 16 and 18. The digitized signals are provided toa data processing device 26. Data processing device 26 may comprise, for example, a programmable device which obtains an estimated blood pressure from characteristics of first and second signals 16 and 18 Data processing device 26 may comprise a computer/microcontroller/microprocessor/DSP or the like connected to ADC 24 by a suitable interface 25.

Figure 3:
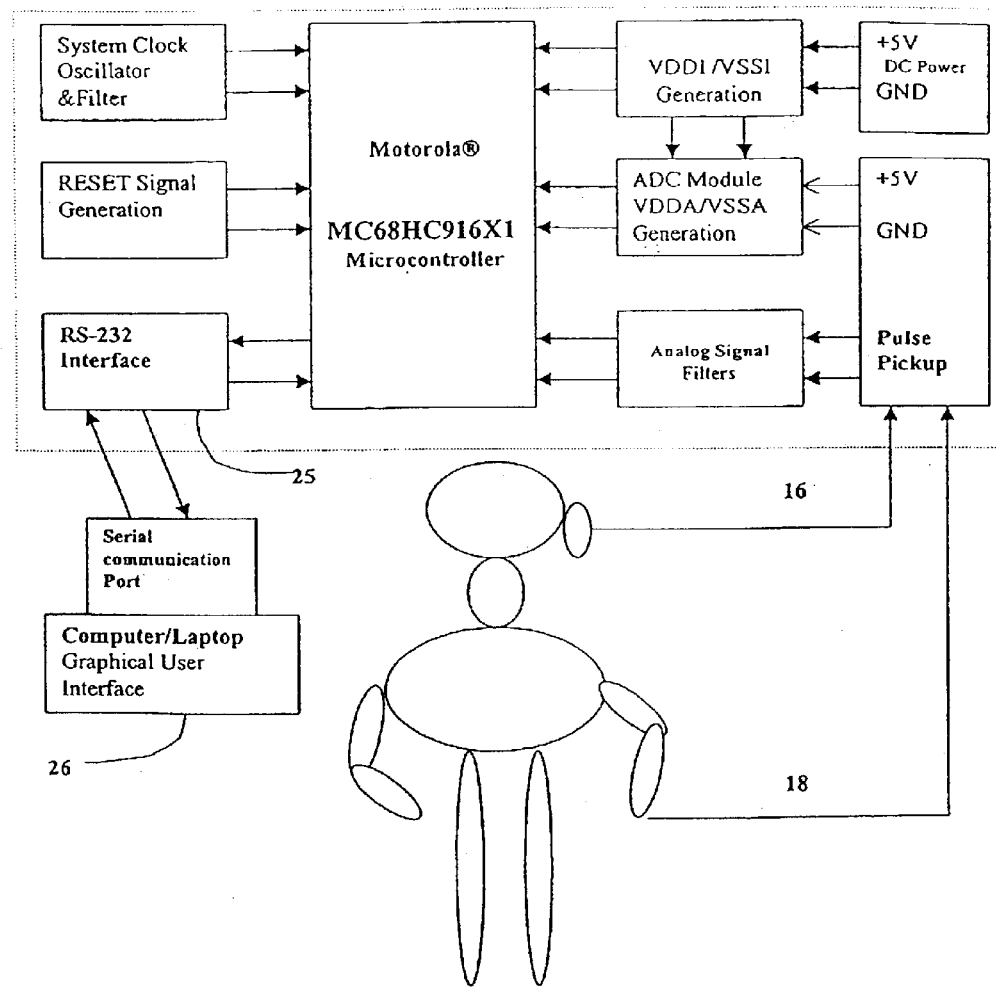
FIG. 3 is a block diagram of apparatus according to one specific embodiment of the invention.

FIG. 3 illustrates apparatus according to a specific embodiment of the invention wherein interface 25 comprise: an RS-232 Aerial interface which receives digitized data from a Motorola MC68HC916X1 microcontroller and transmits that data over a data connection, which may comprise, for example, a standard RS-232 serial cable to the serial port of a data processing device 26. Data processing device 26 may comprise a standard personal computer In the embodiment of FIG. 3, the personal computer is programmed to perform the steps necessary to process digitized signals 16 and 18 to yield estimated blood pressure values. In typical commercial embodiments of the invention processing device 26 is integrated with other parts of system 10 within a common housing and may comprise an embedded processor.

Data processing device 26 determines the time separating selected corresponding locations on the first and second signals 16 and 18. Preferably, processing device 26 determines both the time difference $T_a$ between the peaks of signals 16 and 18 for use in systolic blood pressure estimation and the time difference $T_p$ between the valleys of the first and second signals 16 and 18 for use in diastolic blood pressure estimation.

There are numerous ways in which $T_S$ and $T_D$ can be measured. A preferred method is to use a cross correlation technique. Where two signals are respectively given by $p_1(t)$ and $p_2(t)$ the correlation between the two signals for a time difference of N sample points can be expressed as follows:

$$C_{p1p2}(m) = \frac{1}{N} \sum_{n=0}^{N-m-1} p_1(n)p_2(n+m) \quad (1)$$

The time difference between corresponding points on the two signals is determined by finding the value of m for which the correlation C is maximized and then multiplying by the sampling time $\Delta t$ (e.g. the time between subsequent samples of each signal) as follows;

$$T = m \bigg|_{C \max} \Delta t \quad (2)$$

The sampling time $\Delta t$ may be, for example, 1 millisecond. The sampling time is determined by the sampling frequency.

In general, $T_s$ and $T_D$ are different. One way to separately measure $T_S$ and $T_D$ is to create from signals 16 and 18 a first set of signals $p_1(t)$ and $p_2(t)$ which include the peaks of signals 16 and 18 but do not include the valleys of signals 16 and 18. The cross-correlation between the first set of signals can then be used to obtain a value for $T_a$. Similarly, a second set of signals $p_1(t)$ and $P_2(t)$ which include the valleys of signals 16 and 18 but do not include the peaks of signals 16 and 18 can be cross-correlated to obtain a value for $T_D$. The values for $T_S$ and $T_D$ can be used as described below to compute systolic and diastolic blood pressures, respectively.

The first set of signals can be created from signals 16 and 18, for example, by selecting a threshold for each of signals 16 and 18 with each threshold being lower than the peak values of the signal and setting to a fixed value, such as zero, all data points having values lower than the threshold. A suitable threshold may be derived, for example, by computing the average values of the data points of each of signals 16 and 18 and using these average values as thresholds. Mean values of signals 16 and 18 could also be used as thresholds aid may be considered, for the purpose of this disclosure, to be a type of average value.

The second set of signals can be created from signals 16 and 18, for example, by selecting a threshold for each of signals 16 and 18 with each threshold being higher than the minimum values of the signal and setting to a fixed value, such as zero, all data points having values greater than the threshold. A suitable threshold may be derived, for example, by computing the average or mean values of the data points of each of signals 16 and 18 and using the average values as thresholds. The same or different thresholds may be used in obtaining the first and second sets of signals.

The values $T_S$ and $T_D$ may be obtained from signals 16 and 18 by methods other than computing correlations between signals 16 and 18. For example, peaks or valleys of signals 16 and 18 may be determined by so-called "landmark detection" techniques. Some example landmark detection techniques which may be used in the invention are described in Schneider et al, "A noninvasive EMG technique for investigating the excitation propagation in single motor units," *EMG Clinical Neurophysiology*, Vol. 29, pp.273–280, 1989 which is incorporated herein by reference.

Times $T_S$ and $T_D$ may be used to compute an estimate of a subject's blood pressure. The speed at which pulse waves propagate through a subject's arterial system is related to blood pressure by an equation known as the Moens-Kortweg-Hughes Equation. L. A. Geddes, *Handbook of Blood Pressure Measurement*, Human Press, Clifton, N.J., 1990 describes the theoretical oasis for the variation in pulse propagation speed with blood pressure.

The Moens-Kortweg-Hughes Equation can be expressed as follows:

$$v = \sqrt{(tE0/pd)e^{\lambda P}} = \frac{L}{T} \qquad (3)$$

where v is the pulse wave velocity; t is the thickness of the vessel wall; $E_0$ is the zero-pressure modulus of the vessel wall; ρ is the density of blood; d is the diameter of the vessel; λ is a constant that depends on the elasticity of the vessel; P is a blood pressure within the vessel; L is the distance travelled by a pulse between two points at which a pulse is detected; and T is the time elapsed between detecting the pulse at a first measurement point and detecting the pulse at a second measurement point.

The Moens-Kortweg-Rughes Equation includes a large number of factors which depend upon the elasticity and geometry of a subject's blood vessels. Many of those who have attempted to measure blood pressure by measuring the propagation times of pulse waves have assumed that, over a relevant range, the Moens-Kortweg-Hughes Equation could be expressed as a linear equation. That is, they have assumed that blood pressure and time are related by the following equation over a relevant range of propagation times:

$$P = AT + B \qquad (4)$$

where P and T are as defined above and A and B are parameters which are specific to each individual subject. While the relationship of equation (4) may be used in certain embodiments of this invention, it is not preferred. One problem is that equation (4) generally leads to inaccurate blood pressure estimates in cases where a subject experiences large dynamic fluctuations in blood pressure as can occur in operating room situations.

The inventors have discovered that, for purposes of estimating blood pressure, it is desirable to express the relationship between blood pressure and elapsed lime between detecting pulse signals at two locations L1 and L2 by way of a non-linear function. The non-linear function is preferably generally decreasing and is most preferably monotonically decreasing with increases in T. The non-linear function is preferably concave upward and is preferably specified by a pair of two parameters which can both be adjusted for purposes of calibration. In a preferred embodiment of the invention the non-linear function is generated by the following equation:

$$P = a + b \ln(T) \qquad (5)$$

where P and T are as defined above and a and b are a pair of parameters to be determined for each individual subject by performing a calibration.

The inventors have discovered that the use if a function according to equation (5) for estimating blood pressure provides advantages over methods which use equation (4) for calculating an estimated blood pressure.

In order to use either of equations (4) and (5) to estimate the blood pressure P of a subject from a time difference T it is necessary to obtain values for the constants which are appropriate to the individual in question. Each of equations (4) and (5) includes two constants.

One way to calibrate system 10 for a specific individual is to make measurements of both time T and the subject's blood pressure P (using an alternative blond pressure measurement device such as sphygmomanometer or automatic blood pressure measurement device) at two times when the subject's blood pressure is different. At least two measurements are required. This yields two equations which can be solved to obtain the constants a and b (or A and B).

Obtaining measurements of T at times when a subject has different blood pressures is inconvenient. In general a subject's blood pressure will not predictably fluctuate through a large enough range to obtain measurements of T at two different blood pressures within a convenient time.

Various techniques can be used to deliberately alter a subject's blood pressure to obtain two points from which values for the constants a and b (or A and B) can be determined. These include: administering drugs to the subject which have the effect of raising or lowering the subject's blood pressure (i.e. vasoactive drugs) taking measurements both when a limb of the subject is in a raised position (so that the base hydrostatic pressure within the subject's blood circulatory system is increased) and in a lowered position (so that the base hydrostatic pressure within the subject's circulatory system is decreased); or causing the subject to increase the pressure within his or her thoracic cavity by attempting to exhale against a resistance, as described by Inukai et al., U.S. Pat. No. 5,921,936. While all of these techniques may be used in some embodiments of the invention, none is ideal.

Figure 5:
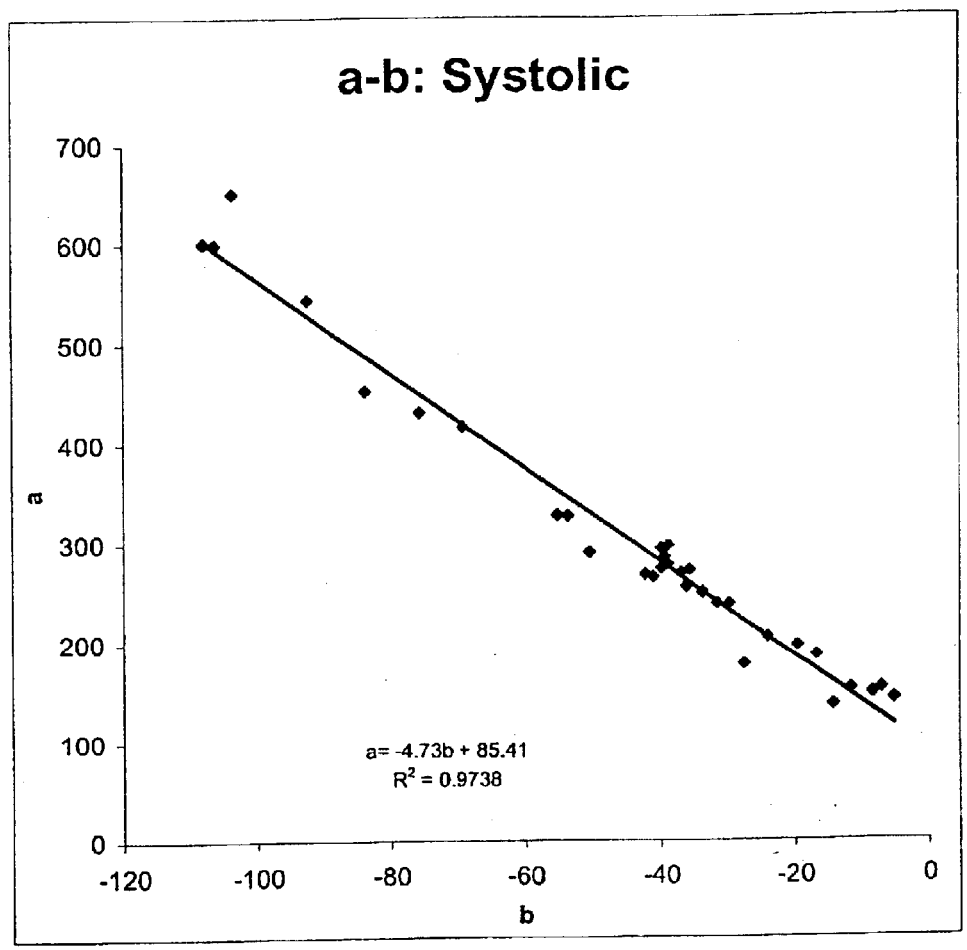
FIG. 5 is a plot of two constants a and b in a formula for estimating systolic blood pressure used in a preferred embodiment of the invention.
Figure 6:
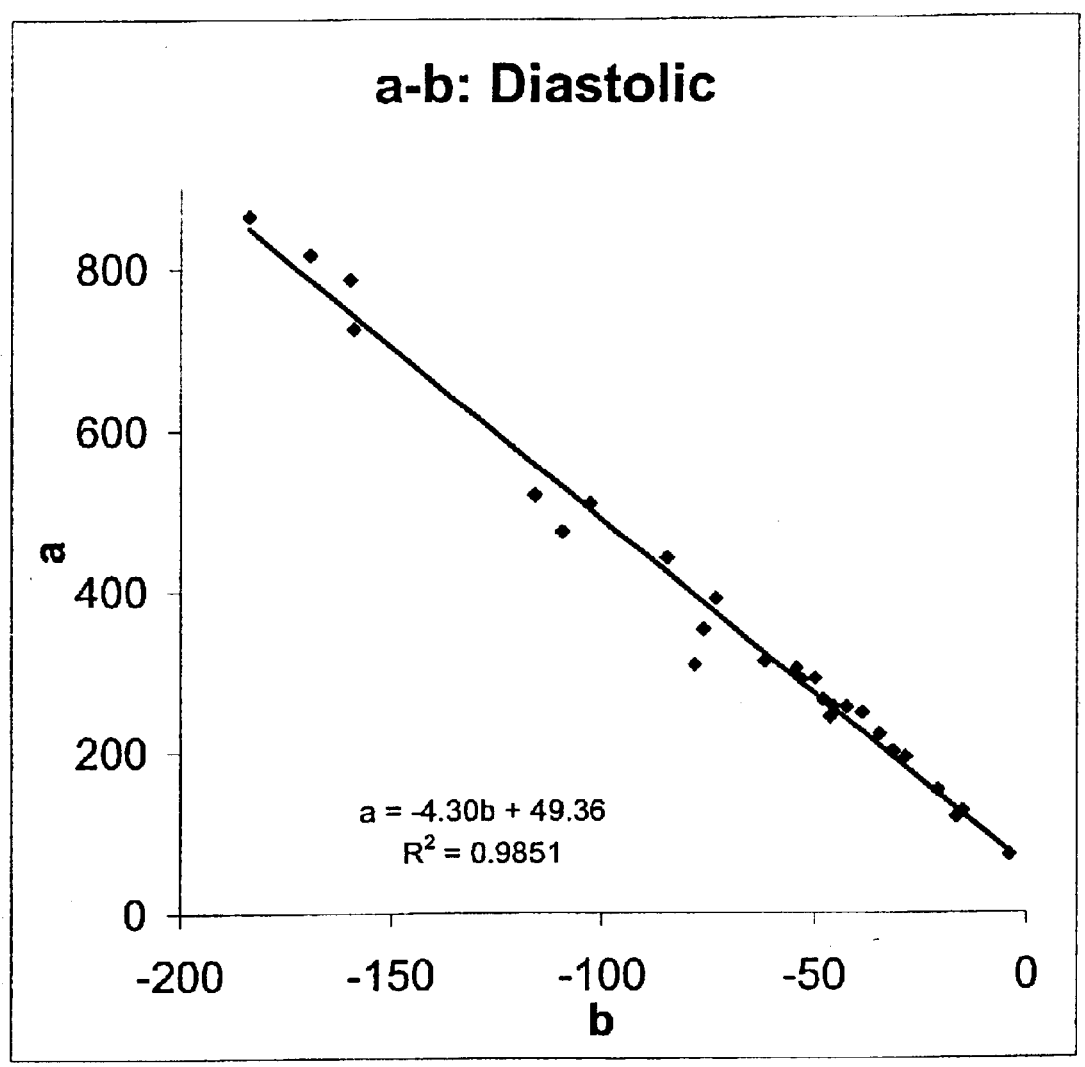
FIG. 6 is a plot of two constants a and b in a formula for estimating diastolic blood pressure used in a preferred embodiment of the invention.

Clinical trials have been conducted to determine the values a and b of Equation (5). The parameters a and b were experimentally measured for a number of subjects. This can be done, for example, by measuring the subject's blood pressure and pulse transit time at a number of different times as the subject's blood pressure varies. Then one can fit the curve of Equation (5) to the data points for each subject to directly obtain values for a and b for that subject. The inventors have discovered that a and b are related generally linearly to one another by the equation:

$$a = c_1 + c_2 b \qquad (6)$$

where $c_1$ and $c_2$ are constants. $c_1$ and $c_2$ are different for systolic and diastolic blood pressure measurements. A plot of the values of a and b for systolic blood pressure measurements made on a number of subjects is shown in FIG. 5. A plot of the values of a and b for diastonic blood pressure measurements made on a number of subjects is shown in FIG. 6.

By taking advantage of the unexpected relationship between a and b, a blood pressure measurement apparatus according to this invention may be calibrated for a specific person using only one set of measurements. Combining equations (5) and (6) gives the relationships:

$$P_S = c_{1S} + c_{2S} b_S + b_S \ln(T_S) \qquad (7)$$

where $P_S$ is estimated systolic blood pressure, and, $$P_D = c_{1D} + c_{2D} b_D + b_D \ln(T_D) \qquad (8)$$

where $P_D$ is estimated diastolic blood pressure. The sets of constants $b_S$, $c_{1S}$, $c_{2S}$ and $b_D$, $c_{1D}$, $C_{2D}$ in equations 7) and (8) are for systolic and diastolic blood pressures respectively. In general, in this disclosure, the subscript S refers to systolic blood pressure and the subscript D refers to diastolic blood pressure.

For systolic blood pressure it has been determined that $c_{1S}$ and $c_{2S}$ are respectively about 85.41 and −4.73 whereas, for diastolic blood pressure, $C_{1D}$ and $C_{2D}$ are respectively about 49.36 and −4.30 when blood pressure is expressed in mmHg, and PTT or DPTT is expressed in milliseconds. Although it is considered best to use the foregoing values, in methods and apparatus of the invention the specific values used for the constants $c_{1S}$ and $c_{2S}$, $c_{1D}$ and $C_{2D}$ may be varied somewhat from these preferred values without departing from the invention. Preferably $c_{1s}$ is in the range of 85±10 and $c_{2s}$ is in the range of −4.7±1. Preferably $c_{1D}$ is in the range 50±10 and $c_{2D}$ is in the range of −4.3±1. It will be appreciated that these constants will vary depending upon the units in which P and T are expressed.

It can be seen that the unexpected correlation between a and b of equation (5) permits system 10 to be calibrated for either systolic or diastolic blood pressure measurements with a single blood pressure measurement made by any alternative reliable method. This calibration process can be done by taking a single reliable measurement of the subject's blood pressure (reference blood pressure, $P_0$) and a corresponding pulse transit time (reference pulse transit time, $T_0$) and calculating the values of a and b for the subject as follows:

$$a = c_1 + \frac{c_2(P_0 - c_1)}{\ln(T_0) + c_2} \tag{9}$$

$$b = \frac{P_0 - c_1}{\ln(T_0) + c_2} \tag{10}$$

where $P_0$ is obtained with a reference blood pressure device; $T_0$ is the measured elapsed time (either $T_S$ or $T_D$) between the detection of a pulse at L1 and the detection of the pulse at L2; and $c_1$ and $c_2$ are as given above.

System 10 may include an input (not shown) for receiving a signal indicative of the reference blood pressure or $P_0$ may be measured using a separate device and entered into system 10 by way of either a data communication interface, or a manual interface (e.g. a keyboard). A reference blood pressure measuring device may also be integrated with system 10.

After system 10 has been calibrated for a particular subject and for a particular pair L1 and L2 of sensor locations then the subject's systolic and diastolic blood pressures can be continuously estimated by frequently measuring $T_S$ and $T_D$, as described above and computing estimated systolic and diastolic blood pressures through the use of the following equation:

$$P = c_1 + \frac{c_2(P_0 - c_1)}{\ln(T_0) + c_2} + \frac{P_0 - c_1}{\ln(T_0) + c_2}\ln(T) \tag{11}$$

Figure 11:
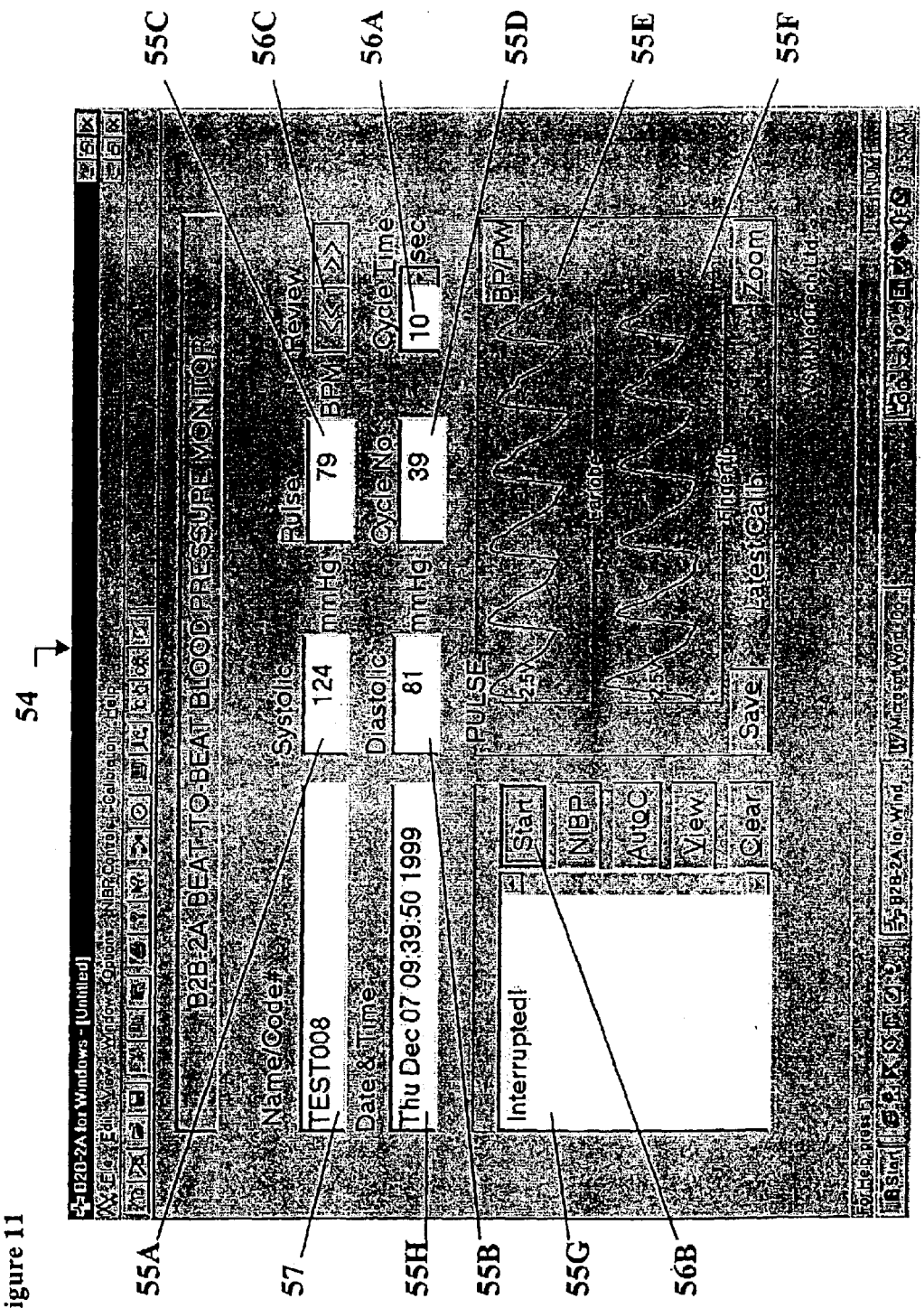

System 10 can then display the subject's estimated blood pressure on a suitable display 54 (FIG. 11), can compare the subject's estimated blood pressure to one or more stored alarm limits and trigger an alarm signal if the estimated blood pressure exceeds or is less than a particular alarm limit, can periodically record the estimated blood pressure(s) for the subject and so on.

Those skilled in the art will understand that equation (5) may be closely approximated by various alternative equations. For example, the relationship between P and T may be represented over a suitable range of values of P by one of the following equations (where $\alpha$, $\beta$, $\delta$ and $\Lambda$ are constant parameters):

$$P = \alpha T^{-\beta} \tag{12}$$

$$P = \delta e^{-\lambda T} \tag{13}$$

The values for the constant parameters in equations (12) and (13) or similar equations may be determined by performing a calibration using experimental data. This may be accomplished, for an individual subject by measuring several pairs of P and T values under conditions such that the subjects' blood pressure is not the same during all of the pairs of measurements. The equation in question can then be fit to the data using a suitable fitting technique such as least-squares fitting.

In general, the parameters of equation (12) (or (13)) are related to one another. This fact can be used to permit single-point calibration of a device which uses one of these equations, or a similar equation, to model the relationship between P and T. The relationship may be derived, for example, by performing calibrations as described in the preceding paragraph, for a significant number of subjects, generating a scatter plot of points $(\alpha, \beta)$ (or $(\delta, \lambda)$) and then fitting a curve to the resulting scatter of points. The curve can subsequently used to predict the value of one of the parameters given a value for the other one of the parameters.

When the values of the constants in Equation (5) (or one of equations (12) and (13)) have been determined (Parameters in equations (12) and (13) may be calibrated from a single or multiple reference blood pressure measurements), then an estimated value for P may be obtained by substituting the measured value for T into the appropriate equation.

In some cases performing calibration as described above can produce erroneous results. This is because no measurement of both a reference blood pressure and a corresponding reference pulse transit time can be precisely accurate. Errors in the values measured for the reference blood pressure and reference pulse transit time may result in significant errors in the values computed for the parameters a and b.

Figure 7:
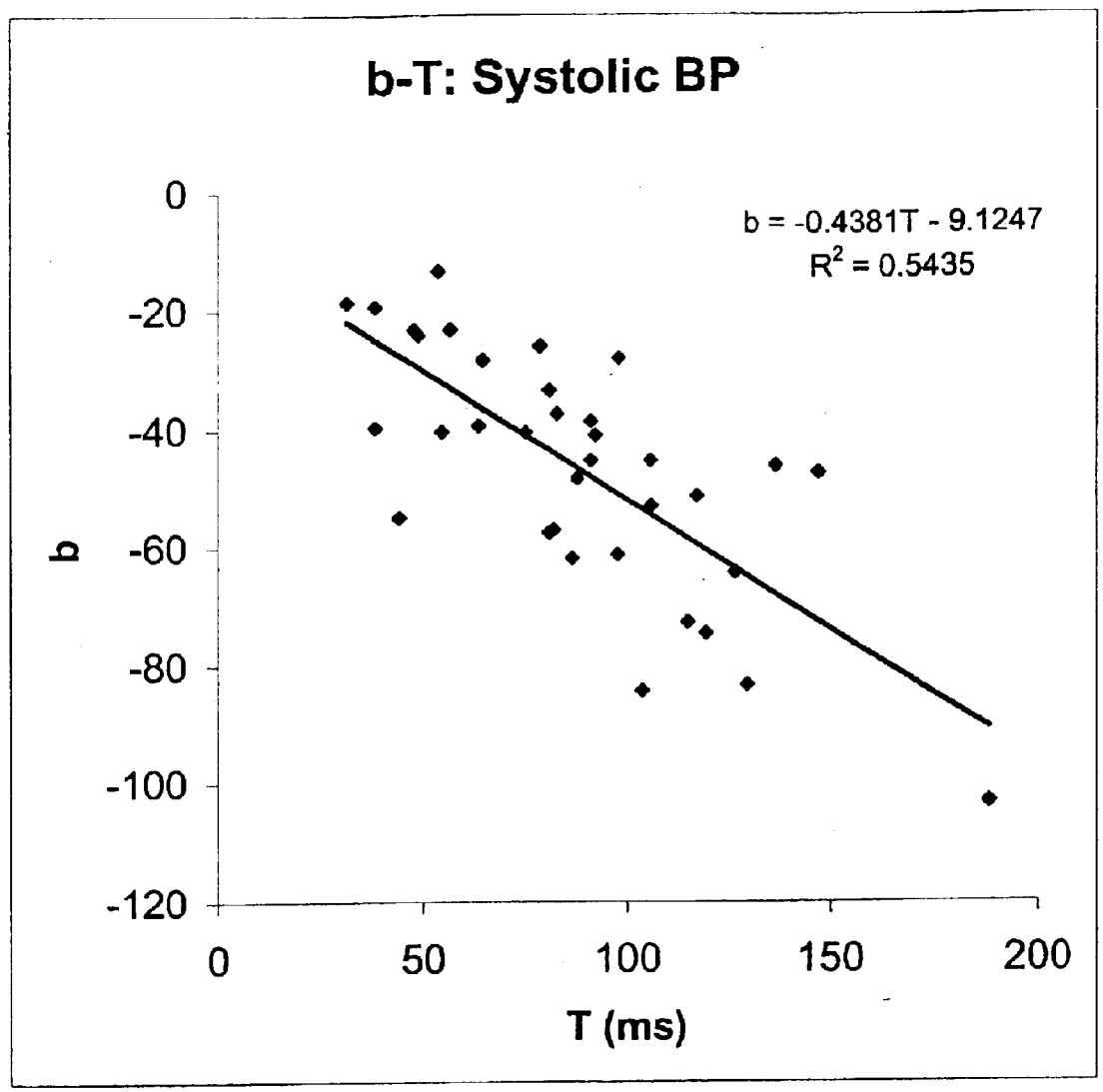
FIG. 7 is a plot illustrating a relationship between the constant b and T which may be taken advantage of in calibrating apparatus according to the invention for measuring systolic blood pressures.
Figure 8:
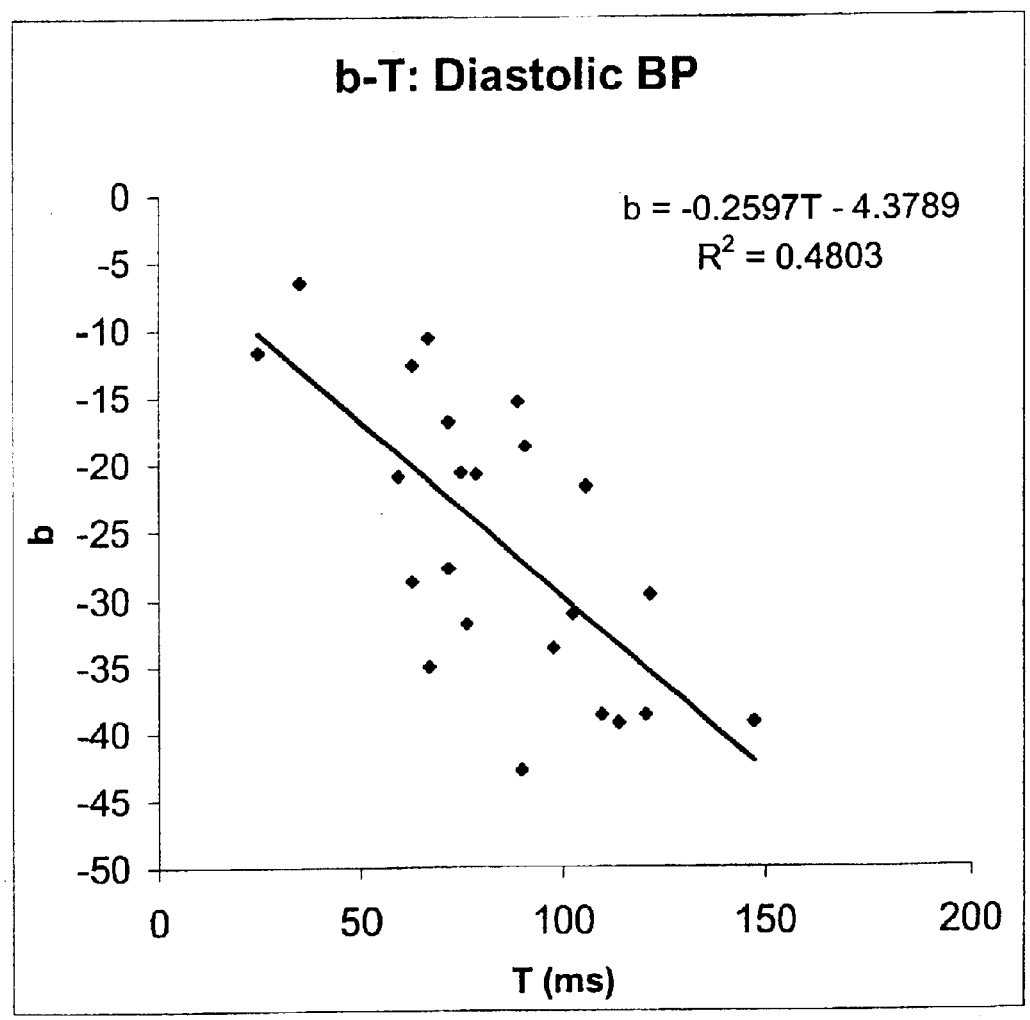
FIG. 8 is a plot illustrating a relationship between the constant b and T which may be taken advantage of in calibrating apparatus according to the invention for measuring diastolic blood pressures.

The inventors have discovered that there is a sufficiently good correlation between the parameter b of Equation (5) and the pulse transit time for use in calibration. This correlation is illustrated in FIGS. 7 and 8 The curves of FIGS. 7 and 8 may be generated by: obtaining multiple P-T data points for each of a number of subjects; obtaining accurate values of a and b by fitting a "best" logarithmic trend line (Equation (5)) to the P-T data points (which may be represented in a scatter chart) for each individual subject; plotting b as a function of $T_a$ for selected subjects (for whom R-squared values for "best" logarithmic trend lines are greater than a suitable value such as 0.5), where $T_a$ is the initial pulse transit time corresponding to the reference blood pressure or the average of all pulse transit time values for each individual subject, and then fitting a suitable curve to the resulting points b-$T_a$ (which may be represented in a scatter chart). It has been found that good results can be obtained when the fitted-curve is a "best" linear trend line, $b = c_3 T + c_4$.

While the linear relationship between the value for b and the pulse transit time $T_a$ is not perfect in is sufficient to permit calibration of system 10. It can be seen from FIGS. 7 and 8 that the relationship between b and $T_a$ is reasonably linear (pairs of b and T were selected with R-squared values for "best" P-T trend lines are typically greater than 0.5). The inventors have found that, for systolic blood pressure, the b-T relationship can be expressed as:

$$b=-0.4381T_a-9.1247 \quad (15)$$

(i.e. $c_{3S}=-0.4381$, $c_{4S}=-9.1247$).

For diastolic blood pressure, the inventors have found that the b-T relationship can be expressed as:

$$b=-0.2597T_a-4.3789 \quad (18)$$

(i.e. $c_{3D}=-0.2597$, $c_{4D}=-4.3789$)

Accordingly, some embodiments of the invention achieve calibration by determining the parameter b (of Equation (5)) from the measured reference differential is pulse transit time $T_0$ according to the appropriate one of Equations (14) and (15). Then, the other parameter a is obtained based on both the reference blood pressure kind reference differential pulse transit time $(P_0,T_0)$ and the relationship of Equation (5).

In particular, a may be obtained as follows:

$$a=P_0-b\ln(T_0)=P_0-(c_3T_0+c_4)\ln(T_0) \quad (16)$$

After system 10 has been calibrated for a particular subject and for a particular pair L1 and L2 of sensor locations using one of the above methods, the subject's systolic and diastolic blood pressures can be continuously estimated by frequently measuring $T_S$ and $T_D$, as described above, and computing estimated systolic and diastolic blood pressure through the use of the following equation:

$$P = P_0 - (c_3T_0 + c_4)\ln(T_0) + (c_3T_0 + c_4)\ln(T) \quad (17)$$
$$= P_0 + (c_3T_0 + c_4)\ln(T/T_0)$$

After the values of the parameters which define the relationship between T and P have been determined, it is not necessary to actually calculate the results of an equation every time that it is desired to make a new measurement of P. After appropriate values for the applicable constants have been determined then any of the above equations can be represented by storing values for P in a lookup table so that the value for P which corresponds to a measured value for T can be obtained by looking up the measured value for T in the lookup table.

Computer software or hardware that uses equation (5), a mathematical equivalent of equation (5), an alternative equation which related P and T in substantially the same manner as equation (5) (such as one of equations (12) or (13)), or a lookup table to obtain a pre-computed value for P from a corresponding value for T may be called a "blood pressure estimation means".

Figure 9:
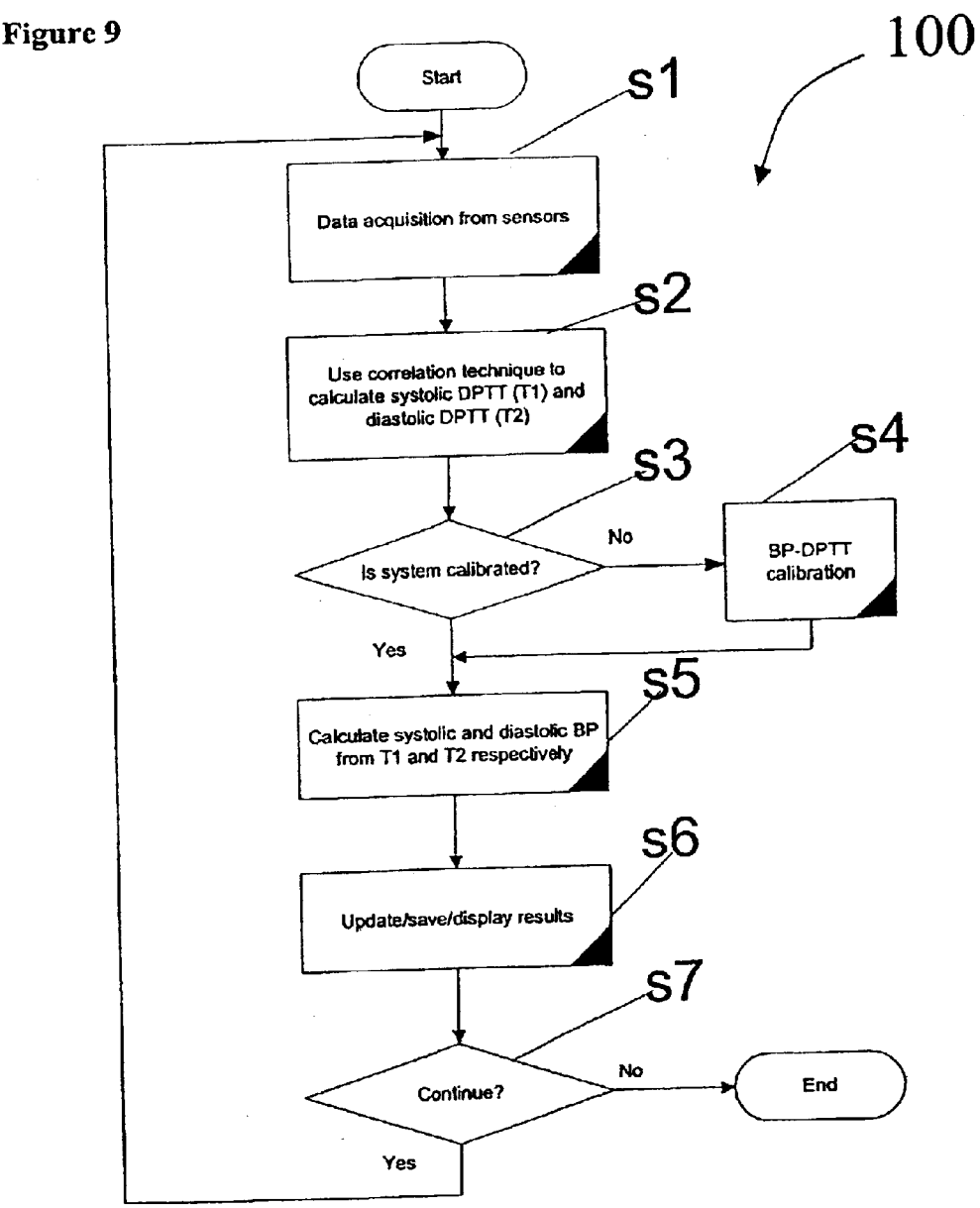
FIG. 9 is a Slow chart illustrating a computer-implemented method for estimating blood pressure according to the invention.

FIG. 9 illustrates a method 100 that may be implemented in device 26 for deriving an estimated blood pressure from first and second pulse signals 16 and 18. device 26 executes software instructions which direct device 26 to request digitized signals is and 18 (block s1). Block s1 may involve device 26 sending a request via interface 25 to ADC system 24 requesting that ADC system 24 obtain and forward by way of interface 25 digitized signals 16 and 18.

In block s2 device 26 is directed to determine $T_a$ and $T_D$ by comparing digitized signals 16 and 18. Block s2 preferably involves computing cross-correlations from signals 16 and 18 as described above.

In block s3, device 26 is directed to determine whether it has calibration information for the current subject. If so then method 100 continues at block s5. If not then method 100 proceeds to block s4 in which device 26 runs computer instructions which cause device 26 to obtain calibration information for the current subject. Such calibration information may be obtained, for example, by requesting and obtaining information identifying a file accessible to device 26 in which calibration information for the subject in question has been stored previously or by requesting input values for measured systolic and diastolic blood pressure from which the values for b can be calculated as described above.

System 10 may include a separate sub-system (not shown) for obtaining reference blood pressure values for calibration purposes. If so, calibration block s4 may include reading a reference blood pressure value from such a subsystem. In the alternative, reference blood pressure values may be entered on a keypad or other user interface.

In block s5 device 26 runs computer instructions which cause it to obtain systolic and diastolic blood pressure estimates from the measured time delay ($T_S$ or $T_D$) using equation (5) above (or an equivalent) and the values for a and b determined in block s4.

In block as device 26 is directed to display computed blood pressure estimates on a suitable display connected to device 26. Block 26 preferably includes saving the blood pressure estimate(s) in a file, and, or otherwise making the blood pressure estimates available for use.

In block s7 data processing device 26 runs computer instructions which determine whether the blood pressure monitoring should continue. Block s7 may include a user selectable delay so that a user can decide how frequently a new blood pressure estimate will be obtained. If device 26 determines in block s7 that a further blood pressure estimate should be obtained then method 100 continues to block s1. If device 26 determines in block s7 that a further blood pressure estimate should not be obtained then method 100 terminates and device 26 awaits further user instruction.

Method 100 may be implemented by running suitable computer software on a personal computer, micro-controller, or other suitable computer device. The computer device may comprise multiple processors. Different steps in method 100 may be performed on different processors.

Method 100 could also be completely implemented in hardware. For example, circuitry for implementing the methods of the invention could be provided on a field programmable gate array ("FPGA") or an application specific integrated circuit ("ASIC"). Apparatus according to the invention may be integrated within a device which performs additional functions. For example, signals 16 and/or 18 could be used to provide data for pulse oximetry determinations and/or pulse rate determinations.

Figure 10:
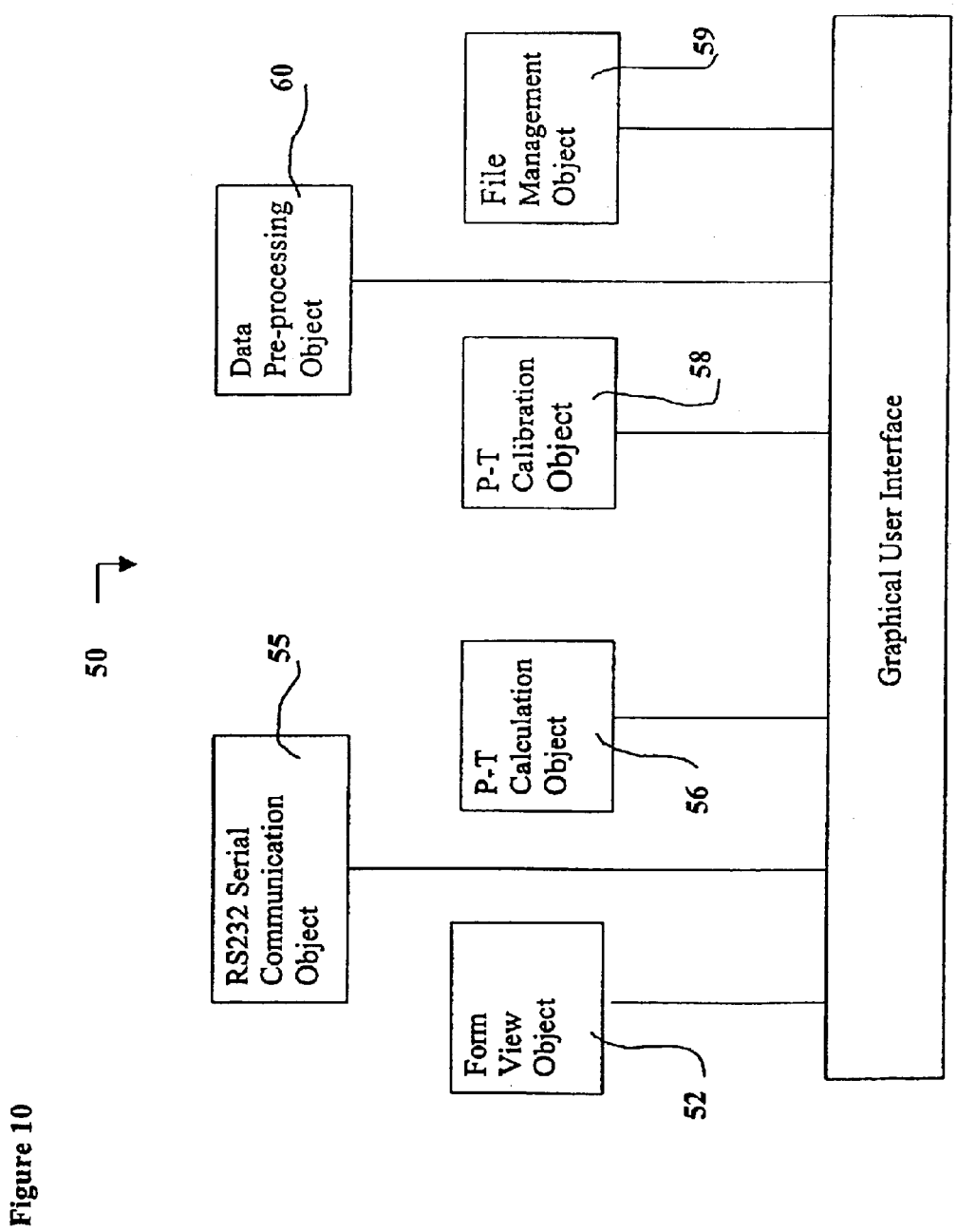
FIG. 10 illustrates a possible organization for software for use in the invention; and, FIG. 11 is a view of a possible user interface display for use in the invention.

FIG. 10 illustrates a possible software architecture for software 50 to be run on a device 26 in the practice of this invention. A form view object 52 provides a graphical display 54 which may, for example, have the appearance shown in FIG. 11. Display 54 provides a graphical user interface by way of which a user can control the operation of system 10 and see the blood pressure estimates developed by system 10. Display 54 includes a portion 55A for displaying estimated systolic blood pressure, a portion 55B for displaying estimated diastolic blood pressure; a portion 55C for displaying the subject's measured heart rate; and a portion 55D for displaying the number of elapsed blood pressure measurement cycles. Portions 55E and 55F show digitized signals 16 and 18. Portion 55G displays status information. Portion 55H displays the current system date and time.

Display 54 may include a number of user controls including a control 56A for setting the cycle time; a control 56B for starting a sequence of blood pressure estimations; a control 56C for reviewing previously recorded blood pressure estimates for the same subject; a portion 57 for setting and displaying the name of the subject being monitored A serial communication object 55 sends commands to ADC unit 24 and receives data from ADC unit 24 via interface 25.

A blood pressure calculation object 56 processes digitized signals 16 and 18 to derive blood pressure estimates, as described above.

A calibration object 58 receives measured blood pressure information and computes parameter values for use in calculating a subject's blood pressure as described above. Calibration object 58 includes, or has access to, calibration information (such as the relationship of Equation (6)).

A file management object 59 moderates the storage of data in files and the retrieval of data from files accessible to device 26.

A data pre-processing object 60 formats the data to be presented in a predefined format, for example a format compatible with application software such as Microsoft™ EXCEL™.

Preferred implementations of the invention comprise a computer processor running software instructions which cause the computer processor to perform a method of the invention. The invention may also be provided in the form of a program product. The program product may comprise any medium which carries a set of computer-readable signals containing instructions which, when run by a computer, cause the computer to execute a method of the invention. The program product may be on any of a wide variety of forms. The program product may comprise, for example, physical media such as magnetic data storage media including floppy diskettes, hard disk drives, optical data storage media including CD ROMs, DVDs, electronic data storage media including ROMs, slash RAM, or the like or transmission-type media such as digital or analog communication links.

As will be apparent to those skilled in the art in the light of the foregoing disclosure, many alterations and modification are possible in the practice of this invention without departing from the spirit or scope thereof. For example, Accordingly, the scope of the invention is to be construed in accordance with the substance defined by the following claims.

What is claimed is:

1. Apparatus for blood pressure measurement, the apparatus comprising:

means for measuring a reference blood pressure $P_0$ and determining a corresponding reference time difference, $T_0$, the time difference representing a difference in time between the arrival of corresponding points of first and second pulse signals at first and second locations respectively;

means for obtaining a non-linear function relating blood pressure and time difference for the subject based upon the reference blood pressure and the reference time difference; and, means for computing an estimated blood pressure, P, at one or more subsequent times, wherein the step for computing the estimated blood pressure includes at least determining a time difference, T, between corresponding points of the first and second pulse signals at the one or more subsequent times and computing the non-linear function of the time difference.

2. A method for obtaining a value representing a blood pressure of a subject, the method comprising:

a step for measuring a reference blood pressure $P_0$ and determining a corresponding reference time difference, $T_0$, the time difference representing a difference in time between the arrival of corresponding points of first and second pulse signals at first and second locations respectively;

a step for obtaining a non-linear function relating blood pressure and time difference for the subject based upon the reference blood pressure and the reference time difference; and, a step for computing an estimated blood pressure, P, at one or more subsequent times, wherein the step for computing the estimated blood pressure includes at least determining a time difference, T, between corresponding points of the first and second pulse signals at the one or more subsequent times and computing the non-linear function of the time difference.

3. A method according to claim 2 wherein the step for obtaining the non-linear function comprises determining at least two parameters of the non-linear function.

4. A method according to claim 3 wherein the step for obtaining the non-linear function comprises determining a first one of the at least two parameters as a predetermined function of the reference time difference.

5. A method according to claim 4 wherein the step for obtaining the non-linear function comprises determining a second one of the at least two parameters based upon the first one of the at least two parameters, the reference blood pressure and the reference time difference.

6. A method according to claim 5 wherein obtaining the first parameter comprises performing the calculation $$b = \frac{P_0 - c_1}{\ln(T_0) + c_2}$$

where $b$ is the first parameter and c1 and c2 are constants, or a calculation mathematically equivalent thereto.

7. A method according to claim 6 wherein obtaining the second parameter comprises performing the calculation:

$$a = c_1 + c_2 b$$

where $a$ is the second parameter, or a calculation mathematically equivalent thereto.

8. A method according to claim 5 wherein obtaining the first parameter comprises performing the calculation:

$$b = c_3 T_0 + c_4$$

where $b$ is the first parameter and c3 and c4 are predetermined constants, or a calculation mathematically equivalent thereto.

9. A method according to claim 8 wherein obtaining the second parameter comprises performing the calculation:

$$a = P_0 - b \ln(T_0)$$

where $a$ is the second parameter, or a calculation mathematically equivalent thereto.

10. A method according to claim 5 wherein the non-linear function comprises a logarithmic function of T and, in the non-linear function, the logarithmic function of T is multiplied by the first one of the parameters.

11. A method according to claim 10 wherein, the non-linear function comprises adding the second one of the parameters to a result.

12. A method according to claim 4 wherein the predetermined function is a function obtained by:

collecting multiple pairs of reference time difference and reference blood pressure for each of a plurality of reference subjects;

for each of the plurality of reference subjects fitting the non-linear function to the multiple pairs of reference time difference and reference blood pressure to obtain values for the first and second parameters for each of the plurality of reference subjects; and, fitting a suitable curve to obtain the predetermined function.

13. A method according to claim 12 wherein the suitable curve comprises a linear trend line.

14. A method according to claim 13 wherein the plurality of reference subjects is selected by picking reference subjects for whom a measure of fit between the non-linear function and the multiple pairs of reference time difference and reference blood pressure exceeds a threshold.

15. A method according to claim 14 wherein the measure of fit comprises an R-squared value.

16. A method according to claim 2 wherein the non-linear function comprises a logarithmic function of T.

17. A method according to claim 2 wherein the value representing a blood pressure of a subject represents a systolic blood pressure of the subject and the corresponding points on the first and second signals are in parts of the first and second signals corresponding to a systolic portion of the subject's pulse.

18. A method according to claim 2 wherein the value representing a blood pressure of a subject represents a diastolic blood pressure of the subject and the corresponding points on the first and second signals are in parts of the first and second signals corresponding to a diastolic portion of the subject's pulse.

19. A method according to claim 2 wherein the non-linear function is a monotonically decreasing function of the time difference.

20. A program product comprising a medium carrying signals embodying instructions which, when executed by a data processor cause the data processor to perform a method according to claim 2.

21. A program product comprising a medium carrying signals embodying instructions which, when executed by a data processor cause the data processor to perform a method according to claim 19.

22. A program product comprising a medium carrying signals embodying instructions, the instructions capable of being executed by a data processor to provide means for measuring a reference blood pressure $P_0$ and determining a corresponding reference time difference, $T_0$, the time difference representing a difference in time between the arrival of corresponding points of first and second pulse signals at first and second locations respectively;

means for obtaining a non-linear function relating blood pressure and time difference for the subject based upon the reference blood pressure and the reference time difference; and, means for computing an estimated blood pressure, P, at one or more subsequent times, wherein the step for computing the estimated blood pressure includes at least determining a time difference, T, between corresponding points of the first and second pulse signals at the one or more subsequent times and computing the non-linear function of the time difference.

* * * * *